(12) United States Patent
Kihm

(10) Patent No.: US 11,058,788 B2
(45) Date of Patent: Jul. 13, 2021

(54) FRAGRANCE DISCHARGE APPARATUS

(71) Applicant: Pium Labs, Inc., Fort Lee, NJ (US)

(72) Inventor: Jaeyeon Kihm, Fort Lee, NJ (US)

(*) Notice: Subject to any disclaimer, the term of this patent is extended or adjusted under 35 U.S.C. 154(b) by 25 days.

(21) Appl. No.: 16/502,880

(22) Filed: Jul. 3, 2019

(65) Prior Publication Data
US 2020/0009284 A1  Jan. 9, 2020

(30) Foreign Application Priority Data

Jul. 4, 2018 (KR) .................. 10-2018-0077441
Jul. 4, 2018 (KR) .................. 10-2018-0077442
Jul. 4, 2018 (KR) .................. 10-2018-0077443

(51) Int. Cl.
*A61L 9/12* (2006.01)
*H04L 29/08* (2006.01)
*H04W 4/80* (2018.01)

(52) U.S. Cl.
CPC .......... *A61L 9/122* (2013.01); *H04L 67/125* (2013.01); *H04W 4/80* (2018.02); *A61L 2209/11* (2013.01); *A61L 2209/132* (2013.01); *A61L 2209/133* (2013.01)

(58) Field of Classification Search
None
See application file for complete search history.

(56) References Cited

U.S. PATENT DOCUMENTS

| 4,111,655 A * | 9/1978 | Quincey ............... A61L 9/122 422/124 |
| 2010/0243754 A1* | 9/2010 | Harris ............... A01M 1/2033 239/34 |
| 2015/0030498 A1* | 1/2015 | Ooten ................. A61L 9/122 422/3 |
| 2017/0253338 A1* | 9/2017 | Fantuzzi ............. B01F 3/04021 |
| 2018/0280557 A1* | 10/2018 | Field .................. B60H 3/0007 |
| 2020/0009285 A1* | 1/2020 | Take .................... A61L 9/14 |

FOREIGN PATENT DOCUMENTS

| JP | 5327416 B2 | 10/2013 |
| KR | 101689763 B1 | 12/2016 |
| KR | 101720266 B1 | 3/2017 |
| KR | 20180055806 A | 5/2018 |

* cited by examiner

*Primary Examiner* — Jelitza M Perez
(74) *Attorney, Agent, or Firm* — Miller & Martin PLLC

(57) ABSTRACT

Provided is a fragrance discharge apparatus. The fragrance discharge apparatus includes one or more fragrance cartridges configured to store a fragrance material; a body to which the fragrance cartridge is mounted; a controller provided in the body to control the discharge of the fragrance material; and a fan configured to mix air and the fragrance material discharged from the fragrance cartridge and make the mixed air flow to the outside of the body.

18 Claims, 17 Drawing Sheets

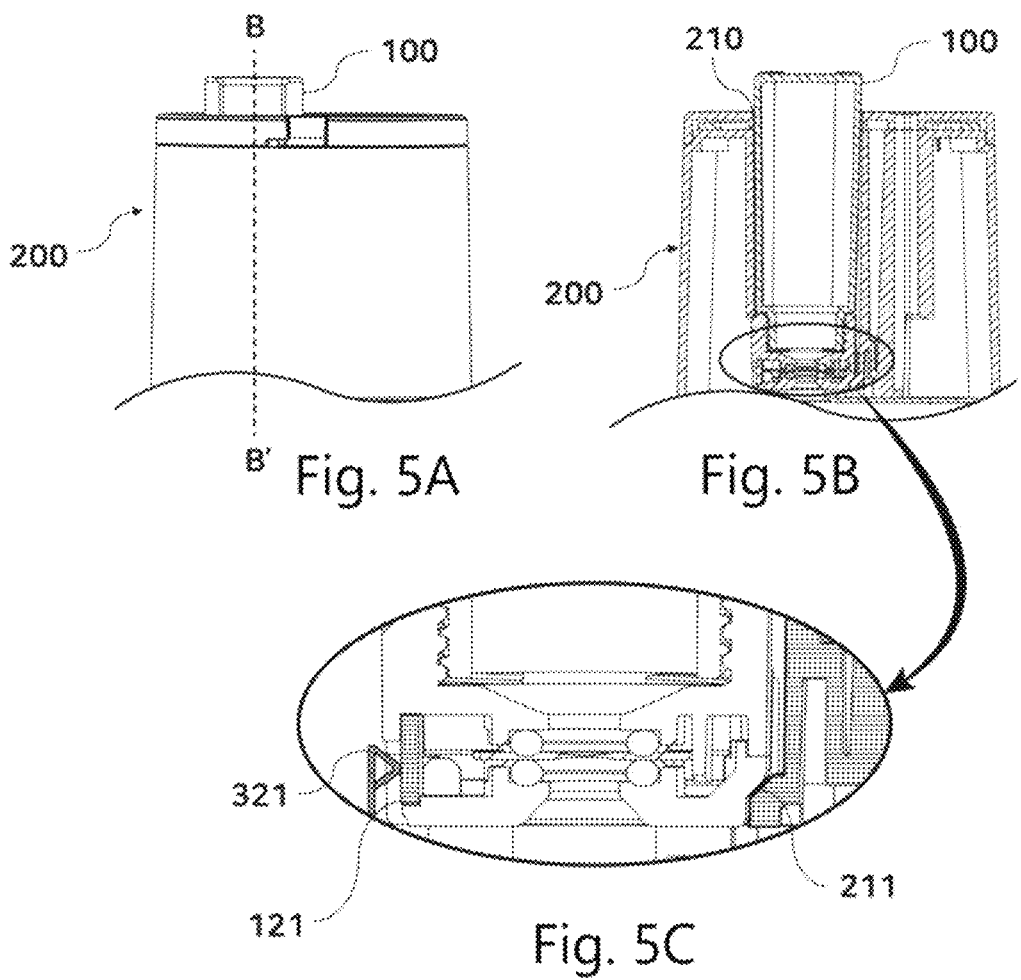

FRAGRANCE DISCHARGE APPARATUS

This application is related to previously filed U.S. application Ser. No. 16/121,268, entitled "Fragrance Discharge Device and Control Method Thereof," U.S. application Ser. No. 16/121,299, entitled "Fragrance Discharge Device," and U.S. application Ser. No. 16/121,309, entitled "Mobile Fragrance Discharge Device," which are herein incorporated by reference in their entirety for all purposes.

TECHNICAL FIELD

Embodiments relate to a fragrance discharge apparatus. The fragrance discharge apparatus manages fragrance cartridges and switches fragrances from the cartridges.

BACKGROUND

A fragrance refers to a pleasant odor that may come from flowers, incense, perfume, etc. It has long been known effect that a specific fragrance may affect psychology and emotions of a user. Therefore, people are using the fragrance for various purposes, such as mood stabilization, psychological stability, and ventilation.

The fragrance is generally provided in a liquid form and may be stored and used in a container provided with a device capable of dispensing liquid. In general, the fragrance in a container is kept at a desired place and used there or by being dispensed by the user over a body part such as a wrist and a neck of the user or clothes of the user, as desired.

However, the fragrance according to the related art is placed a specific space to spread a fragrance within the space through a natural diffusion method or to discharge a fragrance material at designed intervals. Also, the fragrance may be just one kind. To smell another fragrance, the user needs to seal a fragrance bottle or turn a fragrance device off and physically locate another fragrance bottle or switch to another fragrance device.

Also, the user needs to manually match the fragrance to a specific psychological status.

SUMMARY

Embodiments provide a fragrance discharge apparatus that manages the fragrance cartridges and controls the cartridges to switch fragrances.

Embodiments also provide a fragrance discharge apparatus that recognizes the fragrance information in the cartridge, and delivers the information to the users.

Embodiments also provide a fragrance discharge apparatus that changes a discharge pattern and a level of fragrance intensity.

Embodiments also provide a fragrance discharge apparatus that may control more than one fragrance cartridge to provide a fragrance among them or mix more than one fragrances.

Embodiments also provide a fragrance discharge apparatus that may include a mounting hole to place a fragrance cartridge; a shape of the hole may be aligned with a form of the fragrance cartridge to help the user place the fragrance cartridges properly.

Embodiments also provide a fragrance discharge apparatus that may control a fan inside to controls a level of fragrance intensity, a fragrance coverage, and a discharge pattern.

Embodiments also provide a fragrance discharge apparatus that may include a light emitting display configured to provide information about a mounted fragrance capsule or a discharging fragrance capsule.

Embodiments also provide a fragrance discharge apparatus that may further include a light emitting display configured to provide various colors and aesthetic luminous patterns.

There is provided a fragrance discharge apparatus including one or more fragrance cartridges configured to store a fragrance material, a body to which one or more cartridges are mounted, a controller configured to discharge the fragrance material, and a fan configured to discharge the fragrance material that one or more fragrance cartridges discharge; the controller may further control a discharge quantity of the fragrance material and a speed of the fan.

Also, the mounting hole may be located on a top of the body and the fragrance cartridge is placed in the mounting hole.

Also, the fragrance cartridge may include a connector which is electrically connected to a connector inside the mounting hole; the mounting hole may further include a pressing portion to firmly press the fragrance cartridge connector toward the connector inside the mounting hole.

Also, an exterior form of the fragrance cartridge may further include a geometric shape to hold the fragrance cartridge on a flat surface, and the mounting hole may be configured to the exterior form of the fragrance cartridge.

Also, the geometric shape to hold the fragrance cartridge on a flat surface may include a closed curved surface and a side of the fragrance cartridge surface may be flat.

Also, the fragrance cartridge may include a storage configured to store a fragrance material and an ultrasonic vibrator configured to discharge the fragrance material.

Also, the body may include an air outlet that is configured to discharge the fragrance material.

Also, the fragrance cartridge may discharge the fragrance material toward the fan (the direction 1), and the fan discharge air toward the fragrance cartridge (the direction 2); the fragrance material and the air may be blended.

Also, the air outlet on the body is configured to discharge the blended air and the fragrance material in the direction 3 that is not the direction 1 and not the direction 2.

Also, the body may include an air flow duct internally which is configured to guide the air from the fan.

Also, the air flow duct may be a funnel shape which is configured to cause cyclonic air flow.

Also, the air flow duct may include a dome-shape protector internally which is configured to protect the fan.

Also, the fan may be located at the bottom of the body where air inlets are provided.

Also, the fan may be located in the center at the bottom of the body and the air inlets may be provided around a boundary of the bottom; the boundary of the bottom with air inlets may be tilted to reserve a room for airflow.

Also, the body may further include one ore more displays that are configured to provide the mounted cartridge information, the discharging fragrance information, and/or the intensity level of the discharging fragrance material.

Also, the displays may further change the level of brightness according to the discharging fragrance material, a blending ratio of the discharging fragrance material, and/or the intensity level of the discharging fragrance material.

A fragrance discharge apparatus according to the embodiments may control the fragrance material that fragrance cartridges discharge and manage the fragrance cartridges.

Also, the fragrance cartridge may contain the stored fragrance material information, and the user can recognize the stored fragrance material information.

Also, the fragrance discharge apparatus may control the discharging patterns and the level of intensity.

Also, the fragrance discharge apparatus may include the mounting hole for fragrance cartridges, and controls discharging patterns of the fragrance cartridges according to the users' preference.

Also, the fragrance discharge apparatus may guide the users place the fragrance cartridges into the mounting hole following the shape of the mounting hole and the shape of the fragrance cartridges.

Also, the fragrance discharge apparatus may control the intensity level of the discharging fragrances and the discharging patterns of the discharging fragrances using the fan inside the body.

Also, the fragrance discharge apparatus may allow users recognize the mounted fragrance cartridges and/or the discharging fragrance material through the light emitting display showing information stored in the fragrance cartridge.

Also, the fragrance discharge apparatus may further provide visual aesthetics through the various colors and luminous patterns on the light emitting display.

BRIEF DESCRIPTION OF DRAWINGS

FIG. 5A illustrates the fragrance cartridge mounted to a body of the fragrance discharge apparatus according to an embodiment.

FIG. 5B is a cross-sectional view along a line B-B' of the body mounting the fragrance cartridge according to an embedment.

FIG. 5C is a magnification of the cross-sectional view along a line B-B'

DETAILED DESCRIPTION

Figure 1:
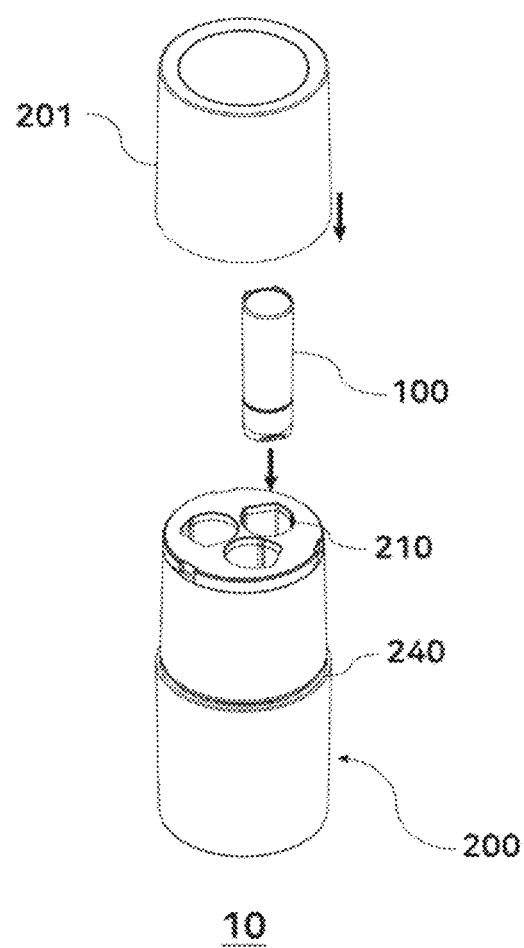
FIG. 1 is a combined perspective view of a fragrance discharge apparatus according to an embodiment.

Hereinafter, embodiments will be described in detail with reference to the accompanying drawings such that those having ordinary skill in the art to which the present disclosure pertains may easily practice the present disclosure. The present disclosure may, however, be embodied in many different forms and should not be construed as being limited to the embodiments set forth herein. In addition, in the description of the present disclosure, detailed description of well-known related structures or functions will be omitted when it is deemed that such description will cause ambiguous interpretation of the present disclosure.

The terminology used herein is for the purpose of describing particular embodiments only and is not intended to be limiting. As used herein, the singular forms "a," "an," and "the," are intended to include the plural forms as well, unless the context clearly indicates otherwise.

It will further be understood that the terms "comprises," "comprising," "includes," and/or "including," when used herein, specify the presence of stated features, integers, steps, operations, components, and/or parts, but do not preclude the presence or addition of one or more other features, integers, steps, operations, components, parts, and/or groups thereof.

In addition, the components shown in the embodiments are individually shown to represent their unique functions, and it may not mean that the components are composed of separate hardware or software constituent units. That is, each component is described individually for convenience of explanation, and a component may be composed of at least two components or one component may be divided into a plurality of components to perform a function. The embodiments of integrated components and the embodiments of separated components are also included in the scope of the embodiments.

Further, the following embodiments are provided for further clear explanation for those of ordinary skill in the art and thus, shapes and sizes of elements shown in the drawings may be exaggerated for the clear explanation.

Hereinafter, the embodiments will be described with reference to the attached drawings.

Figure 2:
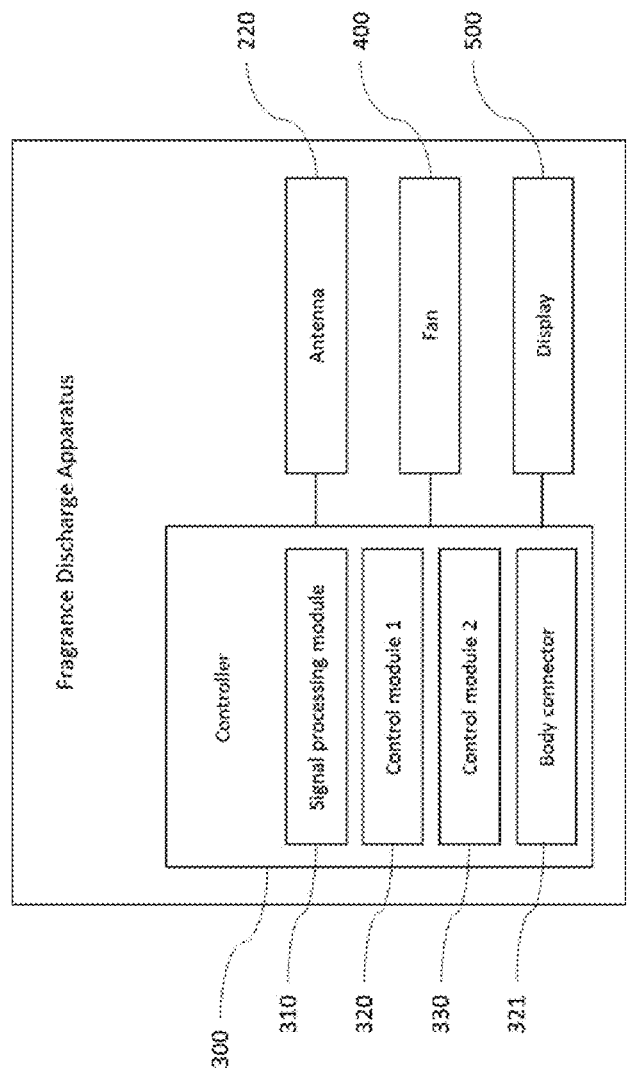
FIG. 2 is a block diagram illustrating a configuration of a fragrance discharge apparatus according to an embodiment.
Figure 3:
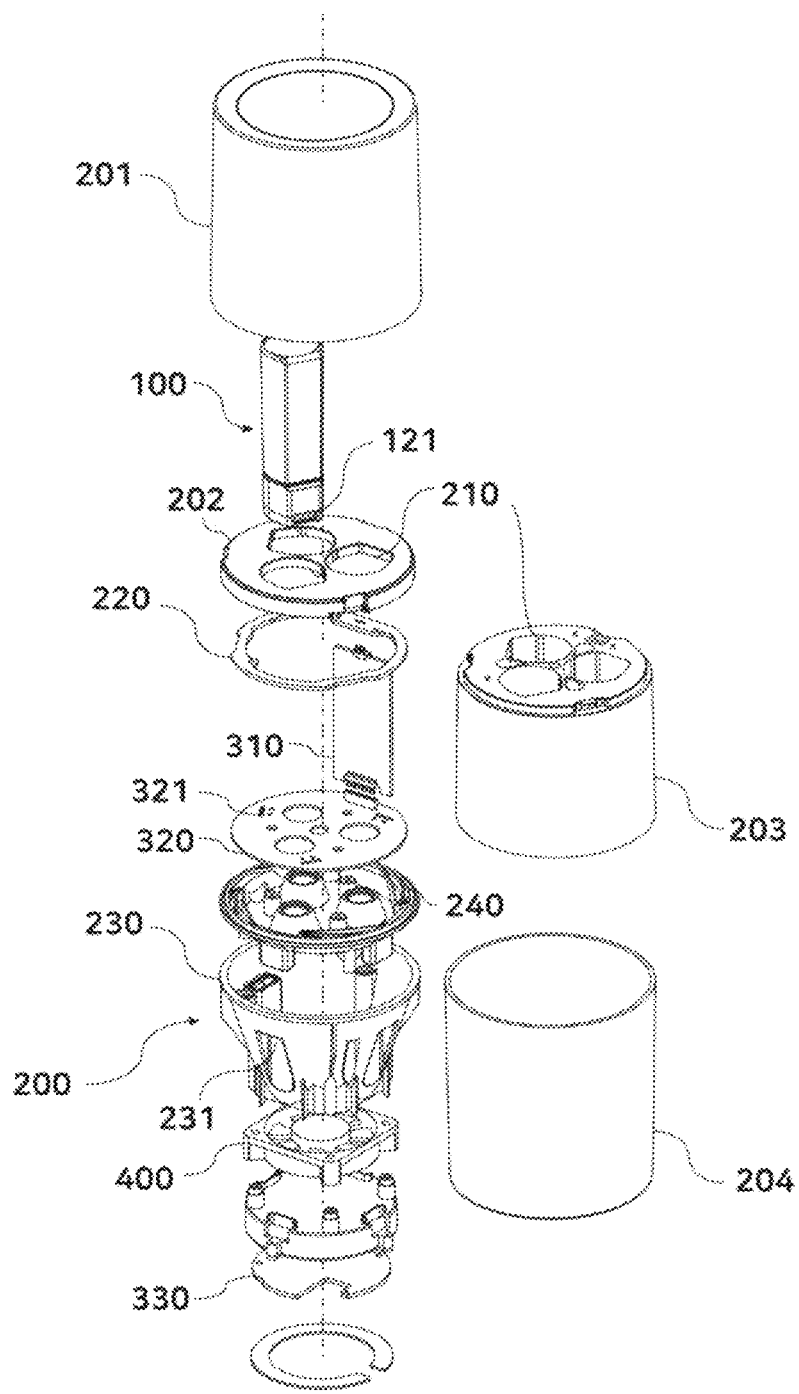
FIG. 3 is an exploded perspective view of the fragrance discharge apparatus according to an embodiment.

FIG. 1 is a combined perspective view of the fragrance discharge apparatus according to an embodiment, and FIG. 2 is a block diagram of the fragrance discharge apparatus according to an embodiment. FIG. 3 is an exploded perspective view of the fragrance discharge apparatus according to an embodiment.

With reference to FIGS. 1 to 3, the fragrance discharge apparatus (10) may comprise one or more fragrance cartridges (100) storing the fragrance material, a body (200) containing the fragrance cartridge (100), a controller (300) provided on the body (200) to control discharge the fragrance material, and a fan (400) included to mix the fragrance material and air, and to discharge the mixed air to the outside of the body (200).

Here, the fragrance material, as substances having a property that can be perceived by the human nose, may be a compound having a scent generally. In general, it is volatile, and it is possible to deliver the scent to human olfactory bulbs. The fragrance material stored in the fragrance cartridge (100) can be liquid, gas, or solid. When the fragrance material are discharged, the fragrance material can be converted to liquid, gas, or solid. For example, the fragrance material stored in the fragrance cartridge (100) may be liquid, but the discharged fragrance material may be gas.

The body (200) has a size and shape capable of accommodating the plurality of fragrance cartridges (100) and the controller (300), and the body may stand on a predetermined area. The body (200) can be formed of a plastic or metal material and can have a cylindrical shape as figures illustrate. The outer shape of the body (200) may be changed in its entire shape, as needed.

On the other hand, the body (200) can be used at a specific place, and can be used on a moving object such as a vehicle. The bottom of the body (200) may have a flat surface to fit within the space.

Also, the body (200) may include a mounting hole (210) containing fragrance cartridges (100). In the embodiment shown in FIG. 1, the mounting hole (210) can be provided, and the body (200) can mount one or more fragrance cartridges (100) storing different fragrance materials. The fragrance cartridges (100) can be replaced to other fragrance cartridges (100).

The body (200) can include a protector (201). The protector (201) can be cylindrical with one side open and hollow. A part of the body (200) including the mounting hole (210) into which the fragrance cartridges (200) are inserted may be inserted into the hollow. The protector (201) covers a part of the body (200) to protect the fragrance cartridges (200) mounted into the mounting hole (210) from damages and contaminants from outside. In addition, since the body (200) covered with the protector (201) hides the fragrance cartridge (200) mounted into the mounting hole (210), the body (200) with the protector (201) can have a seamless and aesthetic external design.

The body (200) can include an antenna (220) inside. The antenna (220) can receive the information stored in the fragrance cartridge (100) by wireless communication. In this embodiment, the fragrance cartridge (100) and the antenna can use the near field communication (NFC). The fragrance cartridge (100) may include an NFC tag, and the NFC tag may store information about the fragrance material stored in the fragrance cartridge (100). The antenna (220) can be seated on the upper housing (203) in an annular plate shape, as shown in FIG. 3, and can be covered by a upper housing cover (202). The fragrance cartridges (100) can be mounted into the mounting hole (210) formed in the upper housing (203) and the upper housing cover (202). Therefore, the fragrance cartridges (100) always passes the inner circumference of the antenna (220) provided between the upper housing (202) and the upper housing cover (203). When the fragrance cartridge (100) passes through the antenna (220), the antenna (220) can read the fragrance information stored on the NFC tag included in the fragrance cartridge (100).

The controller (300) may include a signal processing module (310), a first control module (320), a second control module (330) and a memory (340). The signal processing module (310) can process the signal received from the antenna (220).

The signal processing module (310) may process the fragrance material information received by the antenna (220) from the NFC tag (111) of the fragrance cartridge (100) and send it to the first control module (320). The first control module (320) may receive and process the fragrance material information to which the signal processing module (310) is sent. The first control module (320) may process signals controlling the display (500; see FIG. 10) based on the fragrance material information. Referring to FIG. 11, the antenna (220) and the first control module (320) may be disposed at a certain distance. The signal processing module (310) may then be disposed between the antenna (220) and the first control module (320). If the signal processing module (310) is replaced with the antenna (220) to make the first control module (320) receive and process the signal of the antenna (220) directly, noise may increase according to the position of the antenna (220). Therefore, it is preferable that the first control module (320) receives the signal processed by the signal processing module (310) closely located to the antenna (220), and this may be the optimized circuit arrangement to reduce noise.

The body (200) may include an air flow duct (230) internally for guiding the flow of air generated by the fan (400).

The body (200) can be provided with an air outlet (240) for discharging the mixed air to the outside. The air outlet (240) connected to the air flow duct (230) can be a passage where the air inside the body (200) can flow out, located at the connection site of the upper housing (203) and the lower housing (204).

The mixed air means the gas in which the fragrance material and air were mixed, as mentioned above.

Figure 4A:
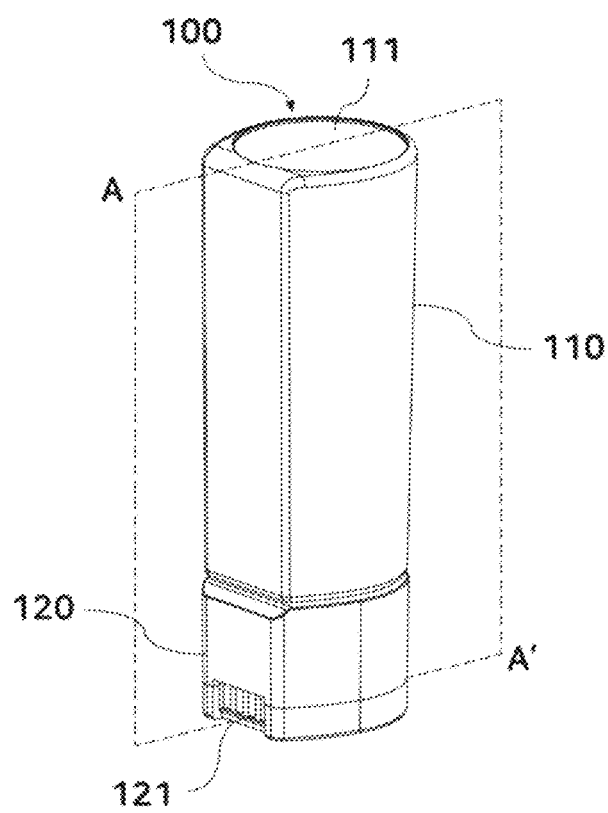
FIG. 4A is a perspective view of a fragrance cartridge according to an embodiment.
Figure 4B:
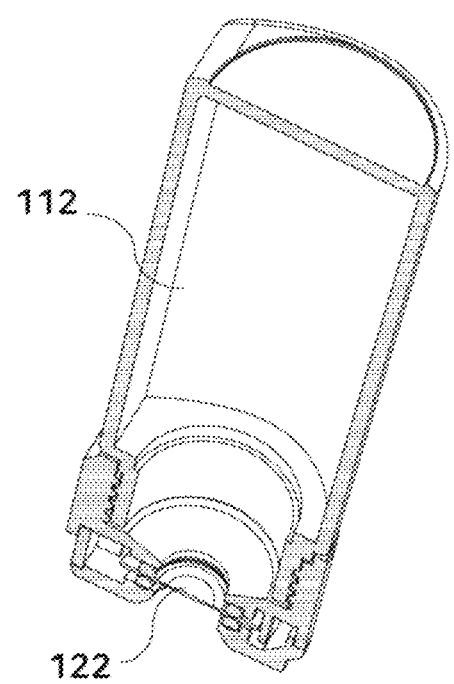
FIG. 4B is a cross-sectional view along a line A-A' of the fragrance cartridge according to an embodiment.

FIG. 4A is a perspective view of the fragrance cartridge according to an embodiment, and FIG. 4B is a cross-sectional view of the fragrance cartridge according to an embodiment.

Referring to FIGS. 4A and 4B, the fragrance cartridge (100) includes an fragrance storage (110) and a fragrance discharger (120). The fragrance storage (110) may include an NFC tag (111) and a container (112). The NFC tag (111) may be prepared on the fragrance storage (110). The container (112) may contain the fragrance in the vacant space provided in the fragrance storage (110). In the NFC tag (111), information of the fragrance stored in the container (112) is recorded or stored. The information recorded or stored in the NFC tag (111) can be read by the antenna (220) shown in FIG. 3.

The fragrance discharger (120) can include a cartridge connector (121) and an ultrasonic vibrator (122). The cartridge connector (121) can be connected to a body connector (321) shown in FIG. 5, and can transmit and receive electrical signals between the fragrance cartridge (100) and the body (200). The ultrasonic vibrator (122) can generate vibration and ultrasonic waves using an ultrasonic transducer. The generated ultrasonic waves can discharge the fragrance material contained in the container (112) in the form of fine particles through the ultrasonic transducer mesh. The fine particles of the fragrance material can be discharged out of the fragrance cartridge (100) and structurally directed to the air flow duct (230) of FIG. 3.

The controller (300) is electrically connected to the fragrance cartridge (100) through the contact of the connector (321) of the body unit and the cartridge connector (121) to send a control signal to the fragrance cartridge (100). The controller (300) transmits the control signal corresponding to the discharge pattern to the fragrance cartridge (100), and the ultrasonic vibrator (122) can control the discharging intensity level of the fragrance material stored in the container (112) according to the received control signal. The ultrasonic vibrator (122) is located at the lowermost portion of the fragrance cartridge (100), and the inside of the fragrance discharger (120) is inclined in the direction from the container (112) to the ultrasonic vibrator (122) in order to discharge the fragrance material contained in the container (112) with no or minimal fragrance material remaining in the storage unit.

The fragrance storage (110) and the fragrance discharger (120) may be screwed together. The outer shape of the combined fragrance cartridge (100) may be directional to prevent rotation. Here, the anti-rotational shape may have a closed curved surface, and one side may be flat. If the cross section of the fragrance cartridge (100) is circular, it can be rotated and it can be difficult to identify which direction. However, if most of the appearance is a curved surface and a part has a flat surface, the insertion direction of the fragrance cartridge (100) can be specified.

Here, it is an example explained in an embodiment that the external shape of the fragrance cartridge (100) is a closed curved surface and one side surface is a plane. Without being limited to this, due to the different graphical nature, it is possible that the difference in which a single direction can be specified has been initiated.

In the present embodiment, it is possible to distinguish a specific direction through the difference in the external shape of the fragrance cartridge (100), that is, the planar portion of the fragrance cartridge (100). Some sides of the specific direction of the mounting hole (210) may be planar so that the mounting hole (210) also correspond to the outer shape of the fragrance cartridge (100). The external shape of the fragrance cartridge (100) and the shape of the mounting hole (210) can guide or force a user to insert the fragrance cartridge (100) into the mounting hole (210) appropriately. Thereby, the body connector (320) of the first control module (320) and the cartridge connector (121) can be in contact with each other.

Referring to FIGS. 3 and 4, the body connector (321) provided in the first control module (320) may be located at the boundary portion of the first control module (320). A cartridge connector (121) may be prepared on the flat side of the fragrance cartridge (100). The shape of the mounting hole (210) can be formed such that the flat side faces the outer shell of the body (200). Such a structure can expose the cartridge connector (121) to the outer shell when the fragrance cartridge (100) is inserted into the mounting hole (210), and place the nozzle of the fragrance cartridge (100) in the central area of the body (200). Also, the signal processing module (310) connecting the antenna (220) and the first control module (320), and one ore more wires connecting the first control module (320) and the second control module (330) are may be located in the boundary area inside the body (200). The wires may pass through the air flow duct (230). The air flow duct (230) may be formed with a connector (231) for passing the wires at an outer portion in the body (200). One or more connectors (231) can be formed in the boundary portion of the air flow duct (230). Since the setting for connection between each element of the controller (300) is arranged in the boundary area inside the main part (200), and it reserves the maximized space in the central portion inside the main part (200).

The first control module (320) and the second control module (330) can be connected to the connection wire to transmit and receive electrical signals. The second control module (330) can control the fan (400) based on the information transmitted from the first control module (320). The second control module (330) includes a power supplier and can transmit received power to each element. The memory (340) may store user specific information and the cartridge information of the fragrance material mounted onto the body (200). Here, the user-specific information may be a record that the user has used the fragrance discharge apparatus (10) so far. For example, the type of fragrance material used, the color assigned to the type of fragrance material, the discharge amount up to the present, and the discharge pattern of the fragrance material. The controller (300) can control the discharge pattern of the fragrance material based on the information related to the user.

The cartridge connector (121) is located on the flat side of the fragrance cartridge (100), and the body connector (321), as it must be in contact with the cartridge connector (121), can be provided at a position on the first control module (320) corresponding to the cartridge connector (121).

FIG. 5A illustrates a fragrance cartridge inserted into a body according to an embodiment. FIG. 5B is a cross-sectional view along a line B-B' of the body mounting the fragrance cartridge according to an embodiment. FIG. 5C is an enlarged view of the cross-sectional view along a line B-B'.

Referring to FIGS. 5A or 5C, the fragrance cartridge (100) may be inserted into the mounting hole (210) of the body (200). The height of the fragrance cartridge (100) may be greater than the depth of the mounting hole (210). Thus, a portion of the fragrance cartridge (100) inserted into the mounting hole (210) can be exposed over the mounting hole (210). The portion of the fragrance cartridge (100) is exposed in order for the user to grip the fragrance cartridge (100), and it makes easier to insert the fragrance cartridge (100) into the mounting hole (210) and remove it from the mounting hole (210).

In the mounting hole (210), a pressing part (211) can be prepared to press the cartridge connector (121) of the fragrance cartridge (100) toward the body connector (321) shown in FIG. 3. The pressing part (211) may apply a force to push the mounted fragrance cartridge (100) toward the body connector (321), when the fragrance cartridge (100) is mounted into the mounting hole (210). Therefore, the cartridge connector (121) is securely contacted to the body connector (321). Also, the structure of the body (200) can wear out on repeated use and removal of the fragrance cartridge (100). The pressing part (211) can prevent a contact failure between the cartridge connector (121) and the body connector (321), which may occur due to the wear of the structure.

Figure 6:
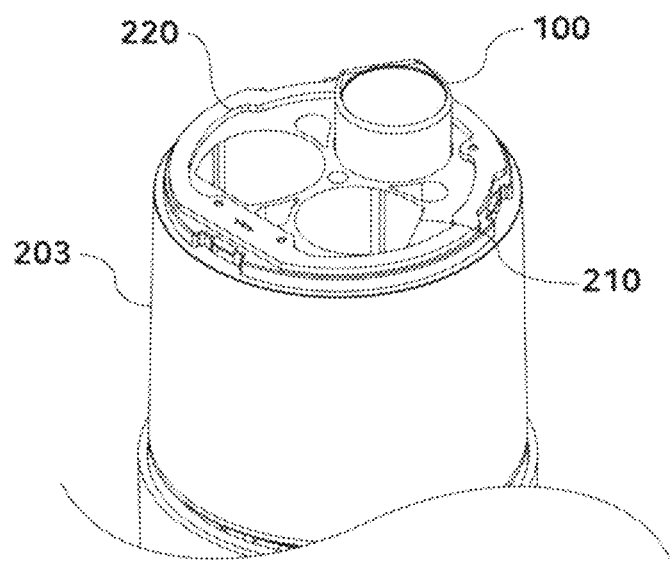
FIG. 6 is an interior view of the fragrance discharge apparatus according to an embodiment.

FIG. 6 is an internal view of the fragrance discharge apparatus according to an embodiment.

Referring to FIG. 6, the antenna 220 may be seated on the top of the upper housing (203) of the body (200). As mentioned above, the antenna (220) can be annular plate shaped. An antenna (220) seated on the upper housing (203) can be around the mounting hole (210). When the fragrance cartridge (100) is inserted or removed from the mounting hole (210), the antenna (220) reads the NFC tag of the inserted and removed fragrance cartridge (100) individually. The mounting hole (210) may be equidistant from the inner circumference of the antenna (220). Since the mounting hole (210) are equidistant from the inner circumference of the antenna (220), the plurality of fragrance cartridges (100) inserted vertically into the mounting hole (210) may also be equidistant from the inner circumference of the antenna (220). An NFC tag storing information of the fragrance cartridge (100) may also be equidistant from the antenna (220). The fragrance cartridges (100) located equidistant from the antenna (220) have similar strengths of the transmission and reception signals between the NFC tag and the antenna (220), thus it can improve the performance of the wireless communication with one or more fragrance cartridges (100).

Here, the positions of the antenna (220) and the fragrance cartridge (100) are not limited to equal distance, but the antenna (220) and the NFC tag of the fragrance cartridge (100) can be located in good distance for wireless communication and one or more fragrance cartridges (100) can be located to minimize signal interference each other.

Figure 7:
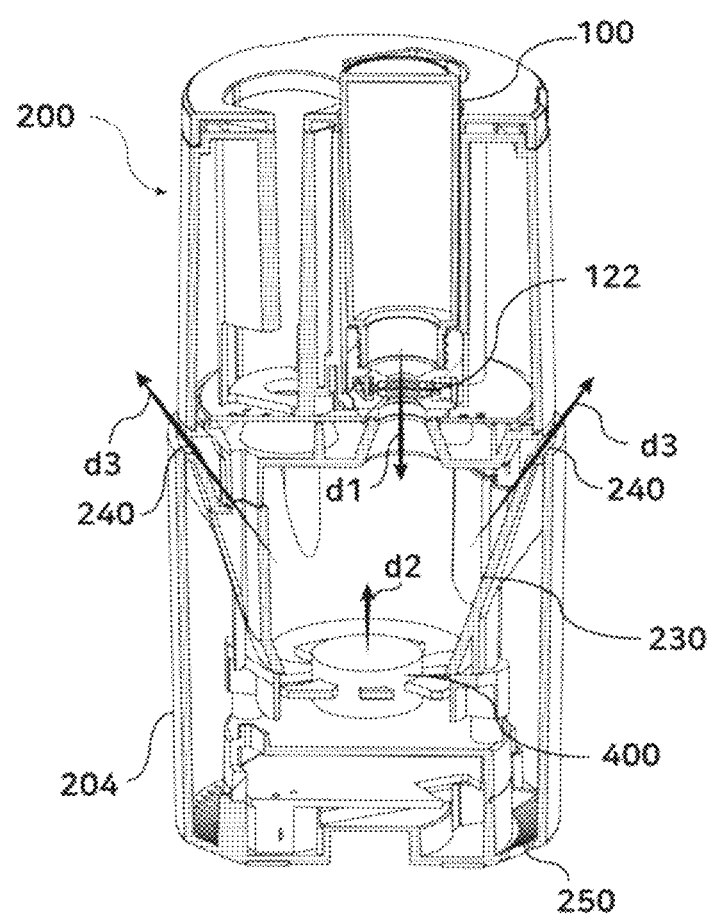
FIG. 7 is a cross-sectional view of the fragrance discharge apparatus according to an embodiment.

FIG. 7 is a cross-sectional perspective view of the fragrance discharge apparatus according to an embodiment.

Referring to FIG. 7, the fragrance cartridge (100) can discharge fragrance in a first direction (d1) towards the fan (400). The fan (400) can cause air to flow in a second direction (d2) towards the fragrance cartridge (100) to mix the fragrance and air. The air outlet (240) may be formed such that the mixture of the fragrance and the air is discharged in a third direction (d3). The air outlet can be formed along the periphery of the body (200) as described above.

The first direction (d1) is the direction from the fragrance cartridge (100) towards the fan (400). The fragrance can be discharged to the air flow duct (230) by the ultrasonic vibrator (122). That is, the ultrasonic vibrator (122) can discharge the fragrance material in the first direction (d1) toward the air flow duct (230) where the fan (200) is located. The fan (400) may be provided at the lower part of the body, and the lower part of the body may be provided with air inlets (250) for allowing external air to flow into the body (200).

When the fan (400) operates, external air can flow into the air flow duct (230) via the air inlets (250). The external air can flow in a second direction (d2) toward the fragrance cartridge (200) by the fan (400). At this time, the fragrance material discharged in the first direction (d1) can meet the outside air directed in the second direction (d2) in the air flow duct (230). A mixture of fragrance and external air can be mixed in an air flow duct (230). The air flow duct (230) may be funnel shaped so that the mixture may cyclonic flow. The spinning mixture can flow in the third direction (d3) toward the air outlet (240) and can be discharged to the outside of the body (200).

Figure 8:
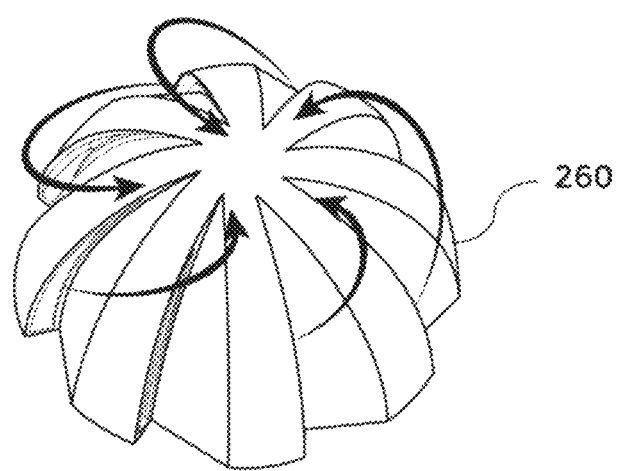
FIG. 8 is a perspective view of a protector included in an air flow duct according to an embodiment.

FIG. 8 is a perspective view of a protector provided in an air flow duct according to an embodiment.

Referring to FIG. 8, a dome shaped protector (260) may be provided inside the air flow duct (230) to protect the fan (400). The protector (260) is installed in the upper portion of the fan (400) and inside the air flow duct (230), so that the air flow generated in the fan (400) can be allowed to flow out while rotating. The rotating and directional air flow can diffuse the mixture evenly in all directions of the air outlet (240). In addition, the protector (260) may be configured to physically protect the fragrance material from the fan (400) and the second control module (330) when the fragrance material is leaking from the fragrance cartridge (100).

Figure 9:
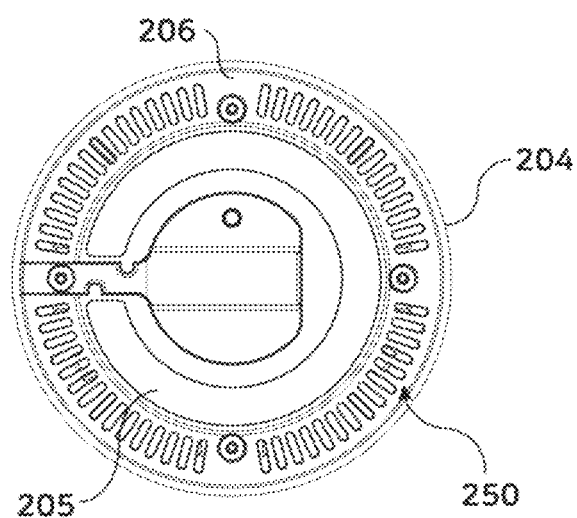
FIG. 9 is a bottom view of the fragrance discharge apparatus according to an embodiment.

FIG. 9 is a bottom view of the fragrance discharge apparatus according to an embodiment.

Referring to FIGS. 7 and 9, the fan (400) may be provided at the center of the lower portion of the body (200). The bottom surface (205) of the lower housing (204) can be provided with inclined surfaces (206) around it. A plurality of air inlets (250) may be formed in a ring along a slope (206) around a fan (400) provided inside the lower housing (204). Since the air inlet (250) is annular along the inclined surface (206), external air can flow smoothly in all directions.

Figure 10:
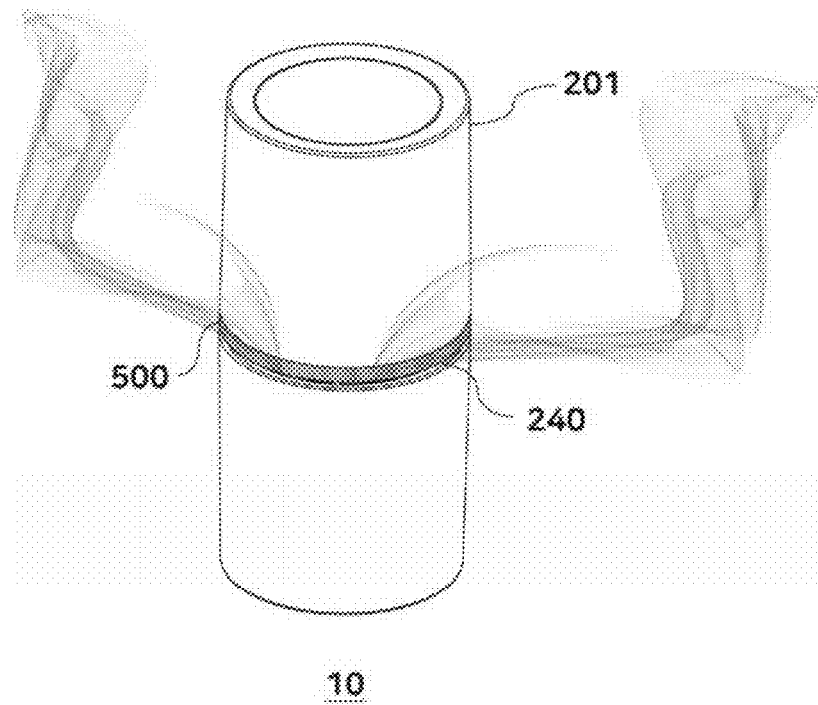
FIG. 10 illustrates examples in which a fragrance discharge apparatus operates according to an embodiment.
Figure 11:
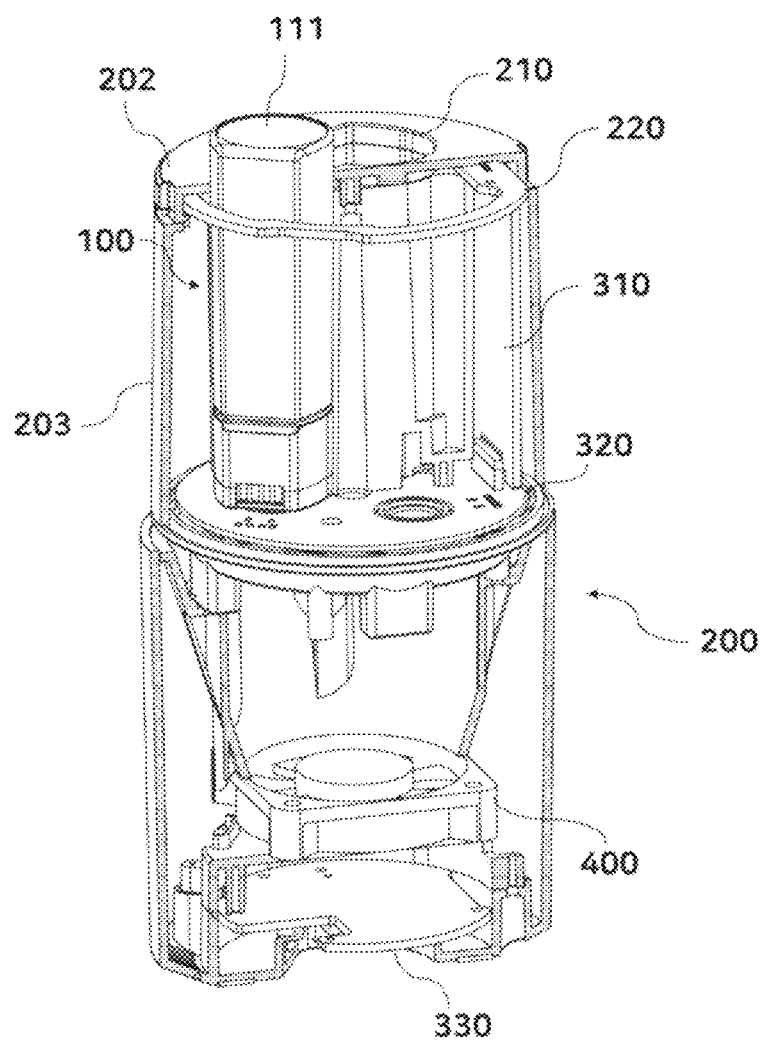
FIG. 11 is a cross-sectional view of the fragrance discharge apparatus according to an embodiment.

FIG. 10 illustrates examples in which the fragrance discharge apparatus according to an embodiment.

Referring to FIG. 10, the fragrance discharge apparatus (10) can include a display device (500). The display device (500) displays information on the fragrance cartridge (100) mounted on the body (200) and the current discharging fragrance material's specific information including fragrance types and the level of intensity. For example, the level of intensity may be determined from a pre-determined volume of fragrance that is discharged by the apparatus.

The controller (300) controls the display device (500) to display predefined color patterns based on the information of the fragrance cartridge (100) mounted on the body (200). When the fragrance cartridge (100) is inserted into the mounting hole (210), the antenna (220) receives the information stored in the fragrance cartridge (100), and the controller (300) recognizes the fragrance material of the fragrance cartridge (100).

The display device (500) displays the predefined color patterns according to the fragrance material in the fragrance cartridge (100) recognized by the controller (300), when the fragrance cartridge (100) is inserted into the mounting hole (210). For example, when the fragrance cartridge (100) containing the lavender fragrance material is inserted to the body (200), the display device (500) can emit purple light. Alternatively, when the fragrance cartridge (100) containing the fragrance material of the rose is inserted the body (200), the display device (500) may emit light in red.

When two or more fragrance cartridges (100) are inserted, the display device (500) may mix the colors assigned to each fragrance material of the fragrance cartridges or emit a pre-defined color.

The display device (500) can emit a pre-defined color pattern according to the fragrance material in the fragrance cartridge (100) recognized by the controller (300), when the fragrance is discharged from the fragrance discharge apparatus (10). That is, when the fragrance discharge apparatus (10) discharges the fragrance material, the display device (500) can emit light in the RGB color assigned to the fragrance material or the fragrance cartridges (100) containing the fragrance material. As an example, with the body (200) mounting the lavender fragrance cartridge and the rose fragrance cartridge are inserted, the display device (500) can emit purple light when the lavender fragrance is discharged, and the display device (500) can emit red light when the rose fragrance is discharged.

When two or more fragrances are discharged, the display device (500) can mix the colors assigned to each fragrance material of the fragrance cartridges or emit a pre-defined color.

In addition, the display device (500) can adjust the brightness of the light according to the intensity level of the fragrance material discharged from the device (10). For example, if the maximum luminance of the display device (500) is 100 lm and the intensity level of the discharging fragrance material is 2 out of 5, the luminance of the display device is 40 lm.

Referring to FIGS. 2 and 5, when the fragrance cartridge (100) is mounted onto the fragrance discharge apparatus (10), the cartridge connector (121) provided in the fragrance cartridge (100) may be in contact with the body connector (321) provided in the first control module (320). When the cartridge connector (121) contacts the body connector (321), an interrupt signal is generated, and the controller (300) can read the information of NFC tag provided in the fragrance cartridge (100) via the antenna (220). Here, the fragrance material information may include the NFC tag ID assigned to each fragrance cartridge (100) and the type of fragrance material contained in the fragrance cartridge (100). The fragrance material is not limited to this.

When the antenna (220) acquires the fragrance material information from the NFC tag (111), the controller (300) compares an existing NFC tag ID with an inserted NFC tag ID to confirm a new NFC tag ID.

When the controller (300) confirms the new NFC tag ID, the controller (300) may transfer a control signal to the fragrance cartridge to discharge the fragrance material in a temporary discharge pattern. Thereby, the user can recognize the new fragrance material when the fragrance cartridge (100) is inserted onto the body (200).

The cartridge (100) can include a cartridge connector (121) and an ultrasonic vibrator (122). The cartridge connector (121) may be in contact with the body connector (321) to transmit and receive electrical signals between the fragrance cartridge (100) and the body (200). The ultrasonic vibrator (122) can generate vibration and generate ultrasonic waves using an ultrasonic transducer. The generated ultrasonic waves can discharge the fragrance material contained in the container (112) in the form of fine particles through the ultrasonic transducer mesh. The particles of the fragrance can be discharged out of the fragrance cartridge (100).

The controller (300) is electrically connected to the fragrance cartridge (100) through the contact of the body connector (321) and the cartridge connector (121) to transmit the control signal to the fragrance cartridge (100). The controller (300) transmits the control signal corresponding to the discharge pattern to the fragrance cartridge (100), and the ultrasonic vibrator (122) can adjust the discharge intensity of the fragrance material contained in the container (112) according to the received control signal. As an example, the control signal may be in the form of an alternating current, and adjust the discharge intensity of the fragrance material by controlling the ultrasonic vibrator (122) by adjusting the frequency of the alternating current.

The controller (300) may control the fan (400) speed based on the discharge pattern of the fragrance material. For example, the controller (300) can increase the fan (400) speed in order to spread the fragrance material broader when a new discharging schedule begins. Since then, the controller (300) can decrease the fan (400) speed to ventilate the inside of the body (200) regularly.

Figure 12:
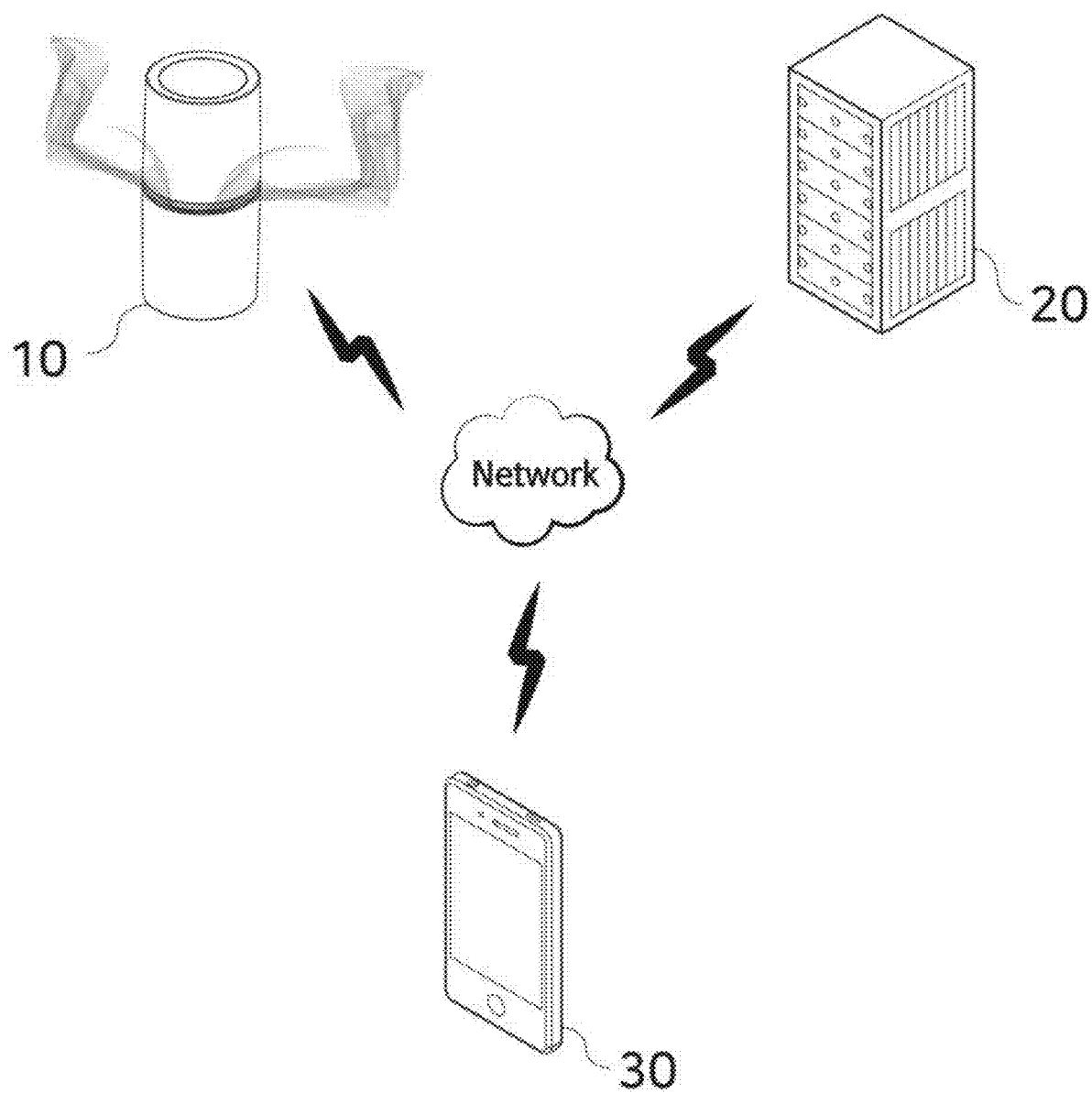
FIG. 12 is a schematic view of a system associated with the fragrance discharge apparatus according to an embodiment.

FIG. 12 is a schematic view of a system associated with an apparatus for the discharge of material in a direction along one embodiment of the present invention.

Referring to FIG. 12, the fragrance discharge apparatus (10) can be connected to a network. The network can be a network such as WIFI, W-CDMA, cdma2000, DV-DO, HSPA, WiBro, LTE, LTE-A, LoRa, NB-IoT, and MQTT. Moreover, it can be a wired communication network connected by wire. The network is not limited to this, and preferably includes technologies to be developed in the future.

A server (20) and a user terminal (30) can be connected to the network. The user can generate his/her ID on the server (20) via the user terminal (30) and register the fragrance discharge apparatus (10). Once the fragrance discharge apparatus (10) is registered, the fragrance discharge apparatus (10) can download user specific information from the server (20) via the network. The information about the user can be updated periodically, if the fragrance discharge apparatus (10) is connected to the network, or upon a request.

The server (20) may transmit the user specific information of the fragrance discharge apparatus (10) to the user terminal (30). The user sees the user specific information of the fragrance discharge apparatus (10) displayed on the user terminal (30) and recognizes the past and current state of the fragrance discharge apparatus (10).

The user can change the user specific information of the fragrance discharge apparatus (10) via the user terminal (30). The user can update an assigned color pattern according to the type of the fragrance material or update the designated discharge pattern via the user terminal (30). The user terminal (30) can transmit the updated user specific information to the server (20) according to the user's input, and the server (20) can transmit the updated user specific information to the fragrance discharge apparatus (10). The user specific information may be stored in a memory (340) of the fragrance discharge apparatus (10). The controller (300) may update the user specific information received from the server (20) and store the user specific information in the memory (340).

Also, the server (20) can transmit recommendation information related to the user to the user terminal (30). The user can confirm the related recommendation information via the user terminal (30), and send the server (20) a request to update the user specific information for the fragrance discharge apparatus (10) to the confirmed recommendation information.

The various embodiments described herein may be implemented by hardware, microcode, software, and/or a combination thereof. For example, various embodiments may include multiple on demand semiconductors (ASICs), digital signal processors (DSPs), digital signal processing devices (DSPDs), programmable logic devices (PLDs), field programmable gate arrays (FPGAs), Processor, controller, microcontroller, microprocessor, other electronic units designed to perform the functions presented herein, or combinations thereof.

Also, for example, various embodiments can be stored and encoded on a computer-readable medium that includes a command. The commands stored or encoded on a computer-readable medium can, for example, implement a method for the programmable processor or other processor when the command is executed. Computer-readable media includes both computer storage media and communication media including any medium that facilitates transfer of a computer program from one place to another. A storage media may be any available media that can be accessed by a computer. For example, such computer-readable media may be RAM, ROM, EEPROM, CD-ROM or other optical disk storage media, magnetic disk storage media or other magnetic storage devices, or any desired program code accessible by the computer Can include any other medium that can be used to convey or store in the form of a command or data structure.

A fragrance discharge apparatus mounting a removable fragrance cartridge for discharging the fragrance material comprising; a body provided with an antenna configured to wirelessly communicate with the fragrance cartridge and a mounting hole configured to mount the removable fragrance cartridge; a controller provided in the body to control the fragrance cartridge by being electrically connected to the antenna, wherein the controller is configured to receive information on the fragrance cartridge via the antenna.

The controller may perform near field communication (NFC; Near Field Communication) with the fragrance cartridge via the antenna.

The antenna has a circular plate shape, and a mounting hole for storing the fragrance cartridge is provided on the body, and the mounting hole is located inside the antenna.

The fragrance discharge apparatus further includes a display for displaying the type of fragrance material stored in the fragrance cartridge and the discharge intensity.

The fragrance discharge apparatus configured to display pre-defined color patterns according to the type of fragrance material stored in the fragrance cartridge and the discharge pattern of the fragrance material.

The fragrance discharge apparatus provided with the controller for receiving the fragrance material information stored in the fragrance cartridge through a wireless communication when the fragrance cartridge is mounted onto the body and controlling the discharge pattern of the fragrance material according to the fragrance cartridge information mounted onto the body and the user specific information.

The fragrance discharge apparatus provided with the controller for transferring the fragrance cartridge information to a server, and receiving the discharge pattern from the server.

The fragrance discharge apparatus provided with the controller for receiving the fragrance cartridge information mounted on the body, and transmitting updated fragrance cartridge information mounted on the body by comparing the mounted fragrance cartridge information with the existing fragrance cartridge information.

The fragrance discharge apparatus provided with the controller for controlling the fragrance cartridge to discharge the fragrance material in a temporary discharge pattern when the fragrance cartridge is mounted first onto the body.

The fragrance discharge apparatus further including a fan for expelling the mixture obtained by mixing the air and the fragrance material discharged from the fragrance cartridge to outside of the body, wherein the fan speed is configured by the controller according to the discharge pattern of the fragrance material.

The fragrance discharge apparatus configured to operate the fan at high speed when discharging the fragrance material, and operates the fan at low speed for ventilating the air inside the body.

The fragrance discharge apparatus configured to discharge the fragrance material using an ultrasonic vibrator in the fragrance cartridge such that the controller controls the frequency of the ultrasonic wave of the ultrasonic vibrator to control the discharge pattern.

The fragrance discharge apparatus provided with the controller including a signal processing module to process the signal received from the antenna.

Figure 13:
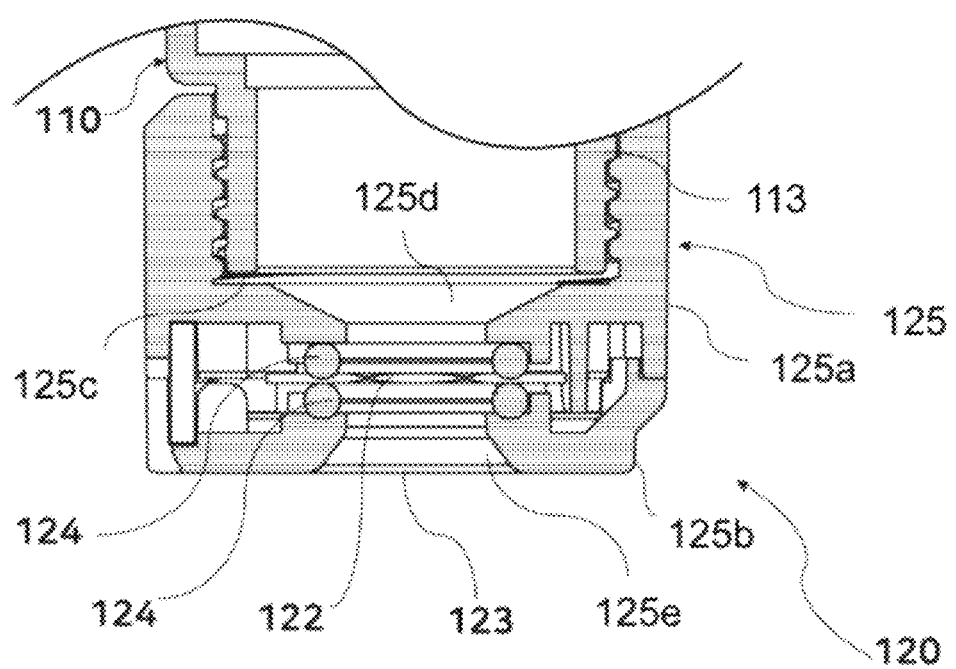
FIG. 13 is a partial cross-sectional view of the fragrance cartridge according to an embodiment.

FIG. 13 is a partial cross-sectional view of the fragrance cartridge according to an embodiment.

Referring to FIG. 13, the housing (125) of the fragrance discharger (120) may be divided into an upper housing (125a) and a lower housing (125b). An ultrasonic vibrator (122) may be prepared between the upper housing (125a) and the lower housing (125b). The upper housing (125a) and the lower housing (125b) can have an open mouth penetrating the center of them. The ultrasonic vibrator (122) may be positioned horizontally in the open mouth. A jaw (125c) may be formed inside the upper housing (125). A lower storage portion (113) of the fragrance storage (110) coupled to the fragrance discharger (120) can arrive at the jaw (125c). Thereby, the fragrance storage (110) can be provided over the ultrasonic vibrator (122).

The lower housing (125b) is provided with a fragrance outlet (123), and the fragrance outlet (123) can be prepared under the lower part (125b) of the fragrance discharger (120). Because the fragrance storage (110) is disposed over the ultrasonic vibrator (122) and the fragrance outlet (123) is located under the ultrasonic vibrator (122), the fragrance material can be supplied to the ultrasonic vibrator (122) by gravity, and the ultrasonic vibrator (122) can discharge the fragrance material below the fragrance discharger (120).

The upper housing (125a) can include a guide funnel (125d). The guide funnel (125d) has a narrower bottom to control the fragrance material stream to the ultrasonic vibrator (122). The guide funnel (125d) can minimize the amount of fragrance material remaining in the fragrance storage (110). The lower housing (125b) can include a diffuser (125e). The diffuser (125e) may have a funnel shape such that the bottom is wider to spread the fragrance material wider following the shape of the diffuser (125e).

A sealing part (124) may be provided between the ultrasonic vibrator (122) and the housing (125). More specifically, a sealing part (124) in the form of an O-ring may be prepared at the portion where the upper housing (125a) and the ultrasonic vibrator (122) are in contact with each other. A sealing part (124) in the form of an O-ring can also be prepared at a portion where the lower housing (125b) and the ultrasonic vibrator (122) are in contact with each other. That is, one sealing part can be prepared on the side of the upper housing upper portion (125a) and one sealing part can be prepared on the side of the lower housing (125b). The sealing part (124) may seal a gap between the ultrasonic vibrator (122) and the housing (121) so that the fragrance material stored in the fragrance storage (110) does not leak to the periphery of the ultrasonic vibrator (122).

Figure 14:
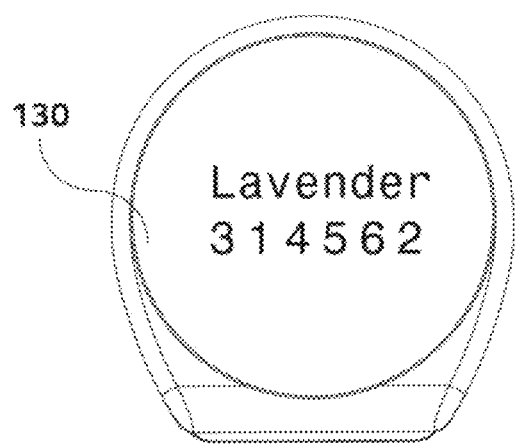
FIG. 14 is a top view of the fragrance cartridge according to an embodiment.
Figure 15:
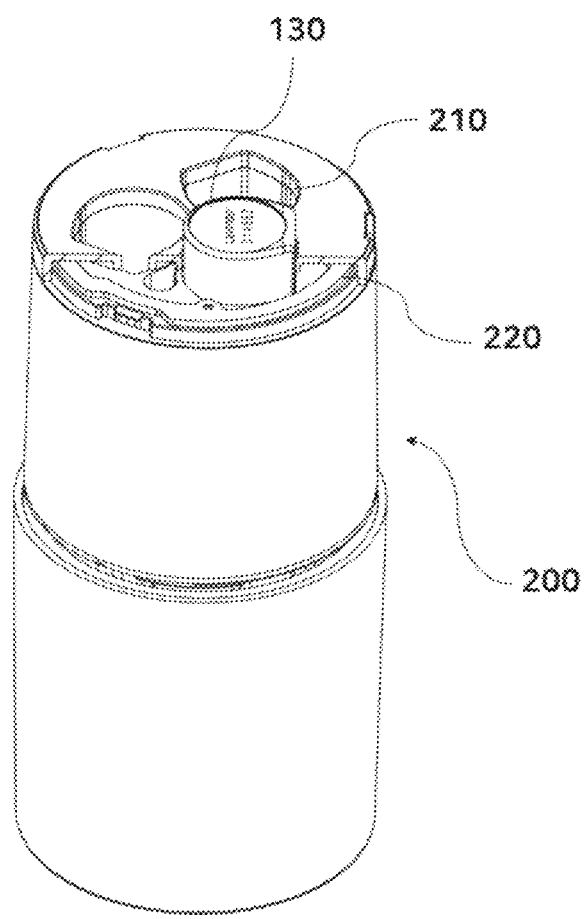
FIG. 15 illustrates the fragrance cartridge mounted on the body according to an embodiment.

FIG. 14 is a plane view of the fragrance cartridge according to an embodiment, and FIG. 15 is a fragrance cartridge mounted on the fragrance discharge apparatus according to an embodiment.

Referring to FIGS. 14 and 15, the fragrance cartridge (100) may include an identification module (130) configured to provide the fragrance material information stored in the fragrance material storage (110) to the fragrance discharge apparatus. The identification module (130) can provide the fragrance material information by wireless communication with the fragrance discharge apparatus. Here, the wireless communication may be near field communication (NFC), and the identification module (130) may be an NFC tag. The NFC tag stores unique ID information, and the ID information can be printed on the identification module (130). The fragrance material information and the ID information can be displayed on the fragrance cartridge (100), and the user can visually recognize the information of the fragrance cartridge (100). The fragrance material may include NFC tag ID information assigned to the fragrance cartridge (100) and the fragrance material contained in the fragrance cartridge (100). The fragrance material information is not limited to this. The fragrance material information stored in the NFC tag can be read by the antenna (220) of the body (200). An NFC tag is an example for storing information related to the fragrance material and providing it passively via the near field communication method. However, the identification module (130) can also actively transmit the fragrance material information using another wired and wireless communication module.

Referring to FIGS. 15 and 5, the fragrance cartridge (100) may be inserted into the mounting hole (210) of the body (200). The height of the fragrance cartridge (100) may be taller than the depth of the mounting hole (210). Thus, a part of the fragrance cartridge (100) in which the fragrance cartridge (100) is inserted into the mounting hole (210) can be exposed. Therefore, the user can grip the exposed part of the fragrance cartridge (100) to insert the fragrance cartridge (100) into the mounting hole (210) or remove the fragrance cartridge (100) from the mounting hole (210).

Figure 16A:
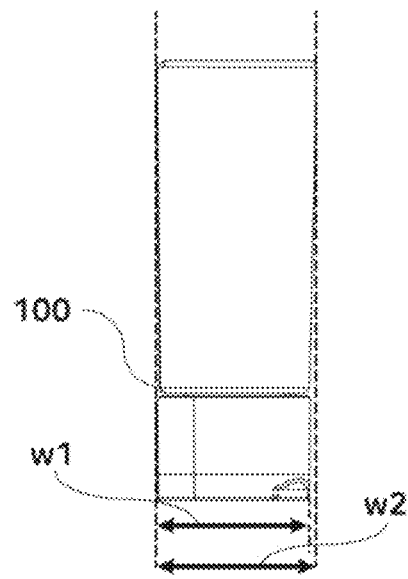
FIG. 16A is a front view of the fragrance cartridge according to an embodiment.
Figure 16B:
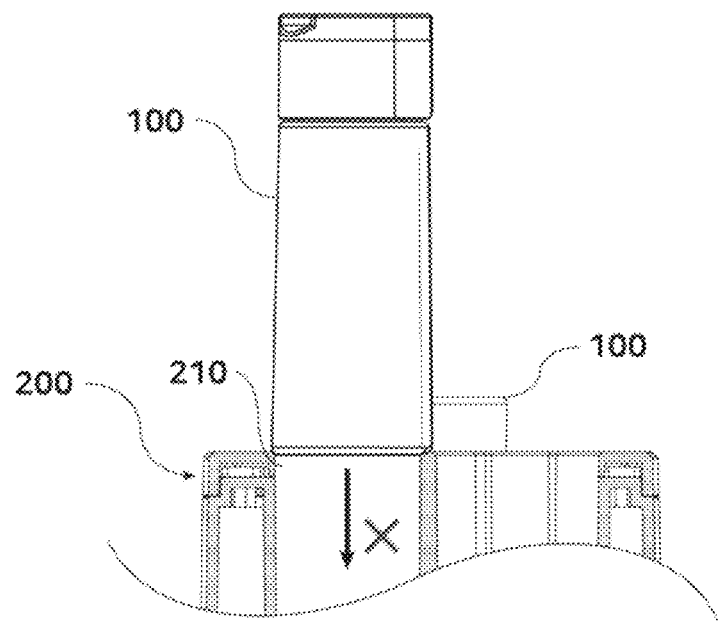
FIG. 16B illustrates the fragrance cartridge inserted in the wrong direction according to an embodiment.

FIG. 16A is a front view of the fragrance cartridge according to an embodiment, and FIG. 16B illustrates the fragrance cartridge inserted in the wrong direction according to an embodiment.

Referring to FIGS. 16A and 16B, the fragrance cartridge (100) has different width of the top of the fragrance capsule (100) and the bottom of the fragrance capsule (100). The cross-sectional diameter (w2) of the top of the fragrance cartridge (100) is the longest, and the cross-sectional diameter (w1) of the bottom of the fragrance cartridge (100) is the shortest.

The structure of the fragrance cartridge (100) can guide the user to insert the fragrance cartridge (100) into the mounting hole (210) of the body (200) in the correct direction. For example, as illustrated in FIG. 6B, when the user inserts the fragrance cartridge (100) upside down, the fragrance cartridge (100) cannot be inserted to the mounting hole (210) because the cross-sectional diameter of the top of the fragrance cartridge (100) (W2) is larger than the cross-sectional diameter of the top of the mounting hole (210). Therefore, the user can recognize that the insertion direction of the fragrance cartridge (100) is incorrect, and try another direction to insert it. For the insertion direction, the fragrance material stored in the fragrance storage (110) can be supplied to the fragrance discharger (120) using gravity.

Figure 17:
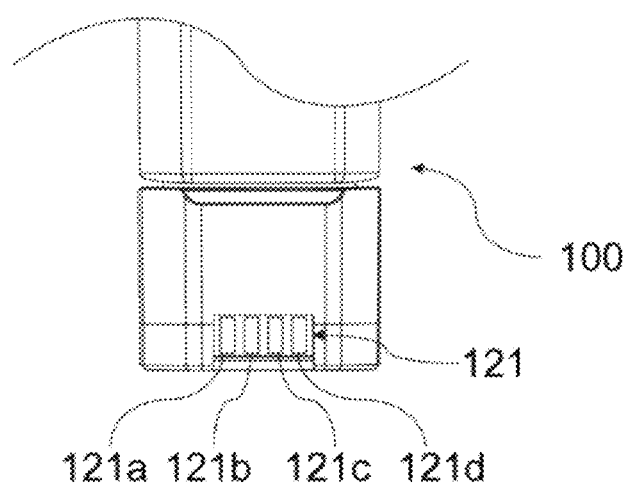
FIG. 17 is a partial view of the fragrance cartridge (100) according to an embodiment.

FIG. 17 is a partial view of the fragrance cartridge (100) according to an embodiment.

Referring to FIG. 17, the cartridge connector (121) of the fragrance cartridge (100) can include four contact terminals (121a, 121b, 121c, 121d). In this embodiment, two (121a, 121b) of the four contact terminals (121a, 121b, 121c, 121d) can be used to receive an alternating current input from the body connector (321) and the remaining two (121c, 121d) can be used to additionally receive signals for impedance or capacitor measurements to measure the remaining amount of the fragrance material in the fragrance storage (110). As a method of measuring the impedance or the capacitor, a capacitance method can be used as an electronic level measurement method. The capacitance method can measure a capacitance value changing according to the level of the fragrance material in the fragrance cartridge (100) with an electrode installed in the fragrance cartridge (100). The capacitance can increase as the fragrance material level rises and decrease as the liquid level descends. The measured value can be converted into a signal by adjusting the output of numerical values of capacitance and impedance electronically.

The number of contact terminals (121a, 121b, 121c, 121d) and the role of each contact terminal is one embodiment, and the invention is not limited thereto. The number of contact terminals can be further increased or decreased as desired, and the role of each contact terminal can be different as required.

A fragrance cartridge mounted in a fragrance discharge apparatus to discharge a fragrance material comprising a storage for storing the fragrance material, and a discharger coupled with the storage for discharging the fragrance material, and the identification module for storing information of the fragrance material in the fragrance cartridge and transmit the information of the fragrance material to the fragrance discharge apparatus.

The fragrance cartridge wherein the identification module is to provide the fragrance material information by wireless communication with the fragrance discharge apparatus.

The fragrance cartridge wherein the identification module is an NFC tag that executes near field communication (NFC).

The fragrance cartridge, wherein the NFC tag stores unique ID information, and the ID information is displayed on the NFC tag.

The fragrance cartridge wherein the discharger includes a housing coupled with the storage, an ultrasonic vibrator mounted in the housing, and the fragrance outlet discharging the fragrance material from the ultrasonic vibrator.

The fragrance cartridge provided with the ultrasonic vibrator located under the storage and over the fragrance outlet discharges the fragrance material which is supplied to the ultrasonic vibrator by gravity.

The fragrance cartridge wherein a guide funnel is formed inside the housing with the narrower cross-sectional diameter at the bottom toward the ultrasonic vibrator.

The fragrance cartridge wherein a sealing part is provided between an ultrasonic vibrator and the housing.

The fragrance cartridge provided with a cartridge connector in electrical contact with the body connector to receive a signal for controlling the discharge of the fragrance material in the fragrance cartridge.

The fragrance cartridge wherein the cartridge connector additionally receives a signal for an impedance or capacitor measurement to measure the remaining amount of fragrance material in the storage.

The fragrance cartridge provided with a structure that the pressing part formed in the fragrance discharge apparatus presses the fragrance connector toward the body connector.

The fragrance cartridge provided with a magnet so that another magnet located in the fragrance discharge apparatus according to the position of the magnet provided in the fragrance cartridge stick together to connect the fragrance connector to the body connector.

The fragrance cartridge wherein the external shape of the fragrance cartridge is radially asymmetric to guide the fragrance cartridge mounting to a mounting hole so that the cartridge connector is connected to the body connector.

The fragrance cartridge is mounted on a mounting hole of the fragrance discharge apparatus, and the height of the fragrance cartridge is larger than the depth of the mounting hole.

The aforementioned description is provided as an example only and thus, one of ordinary skills in the art to which the disclosure pertains may understand that various modifications may be made without departing from the technical spirit or features of the disclosure. Therefore, the aforementioned embodiments should be understood as examples and construed as not be limiting.

The scope of the disclosure is defined by the claims and the equivalents and all of the changes or modifications from the scope of the claims and the equivalents should be understood to be included in the scope of the disclosure.

What is claimed is:

1. A fragrance discharge apparatus comprising:
   a body including a mounting hole for a removable fragrance cartridge, wherein the removable fragrance cartridge is configured to contain a fragrance material;
   a controller configured to control discharge of the fragrance material from the removable fragrance cartridge; and
   a fan positioned such that a generated air flow from the fan mixes air and the fragrance material discharged from the removable fragrance cartridge and expels the mixture outside of the body, wherein the body is provided with an antenna for receiving information associated with the fragrance material stored in the removable fragrance cartridge and transmitting the fragrance material information to the controller, and wherein the antenna has a hollow circular plate shape, and the mounting hole is positioned inside the antenna.

2. The fragrance discharge apparatus of claim 1, wherein the mounting hole is configured to receive the removable fragrance cartridge, and the removable fragrance cartridge and the mounting hole are arranged such that the removable fragrance cartridge can be inserted into and ejected from the mounting hole.

3. The fragrance discharge apparatus of claim 1, wherein the removable fragrance cartridge comprises a cartridge connector configured to electrically connect to a body connector in the mounting hole, and in the mounting hole, a pressing part is configured to press the cartridge connector towards the body connector.

4. The fragrance discharge apparatus of claim 1, wherein a shape of the removable fragrance cartridge is radially asymmetric so as to prevent rotation while mounted onto the body, and a shape of the mounting hole corresponds to the shape of the removable fragrance cartridge.

5. The fragrance discharge apparatus of claim 1, wherein the fragrance discharge apparatus further comprises a transducer.

6. The fragrance discharge apparatus of claim 1,
wherein the controller is further configured to control discharge of the fragrance material from the removable fragrance cartridge to an air duct located in the body below the removable fragrance cartridge;
wherein the fan is positioned below the removable fragrance cartridge such that the generated air flow from the fan mixes air and the fragrance material discharged from the removable fragrance cartridge; and
wherein the body further comprises an air outlet for discharging the mixture outside of the body.

7. The fragrance discharge apparatus of claim 6, wherein the removable fragrance cartridge discharges the fragrance material in a first direction towards the fan, and the fan causes air to flow in a second direction towards the removable fragrance cartridge so as to mix the fragrance material and the air.

8. The fragrance discharge apparatus of claim 7, wherein the air outlet discharges the mixture in a third direction different from the first direction and the second direction.

9. The fragrance discharge apparatus of claim 1, wherein the body further comprises an air flow duct that guides the flow of air generated by the fan.

10. The fragrance discharge apparatus of claim 9, wherein the air flow duct has a funnel-like shape, and is configured to cause the mixed air to flow in a cyclonic manner.

11. The fragrance discharge apparatus of claim 1, further comprising a dome-shape protector between the fan and the removable fragrance cartridge to protect the fan from the fragrance material.

12. The fragrance discharge apparatus of claim 1, wherein the body further comprises air inlets that are positioned at the bottom of the body for allowing external air to flow into the body, and wherein the fan is positioned at the bottom of the body.

13. The fragrance discharge apparatus of claim 12, wherein the fan is disposed substantially at the center of a lower portion of the body, and the air inlets are positioned on an inclined surface of the bottom of the body.

14. The fragrance discharge apparatus of claim 1, further comprising a display for displaying information pertaining to the removable fragrance cartridge mounted on the body.

15. The fragrance discharge apparatus of claim 14, wherein the display adjusts colors and brightness based on the fragrance material and the discharge volume associated with the fragrance material.

16. The fragrance discharge apparatus of claim 1, wherein the controller performs a near field communication (NFC) with the removable fragrance cartridge via the antenna.

17. The fragrance discharge apparatus of claim 1, wherein the controller receives fragrance material information stored in the removable fragrance cartridge through a wireless communication when the removable fragrance cartridge is mounted onto the body and adjusts a discharge pattern of the fragrance material according to the fragrance material information and user specific information.

18. The fragrance discharge apparatus of claim 17, wherein the controller transfers the fragrance material information to a server, and receives the discharge pattern and the user specific information from the server.

* * * * *